United States Patent
de los Reyes

(10) Patent No.: US 10,391,423 B2
(45) Date of Patent: *Aug. 27, 2019

(54) STACKABLE PLANAR ADSORPTIVE DEVICES

(71) Applicant: SPF Technologies LLC, Somerville, MA (US)

(72) Inventor: Gaston de los Reyes, Somerville, MA (US)

(73) Assignee: SPF TECHNOLOGIES LLC, Somerville, MA (US)

(*) Notice: Subject to any disclaimer, the term of this patent is extended or adjusted under 35 U.S.C. 154(b) by 26 days.

This patent is subject to a terminal disclaimer.

(21) Appl. No.: 15/456,484

(22) Filed: Mar. 11, 2017

(65) Prior Publication Data

US 2017/0182433 A1    Jun. 29, 2017

Related U.S. Application Data

(63) Continuation-in-part of application No. 14/907,804, filed as application No. PCT/US2014/050743 on
(Continued)

(51) Int. Cl.
*B01D 15/18* (2006.01)
*B01D 15/20* (2006.01)
(Continued)

(52) U.S. Cl.
CPC ......... *B01D 15/22* (2013.01); *B01D 15/1842* (2013.01); *B01D 15/206* (2013.01);
(Continued)

(58) Field of Classification Search
CPC .. G01N 30/52; G01N 30/6047; G01N 30/482; G01N 30/6043; G01N 30/6069;
(Continued)

(56) References Cited

U.S. PATENT DOCUMENTS 3,340,085 A    9/1967 Halasz Istvan
3,422,604 A    1/1969 Haase
(Continued)

FOREIGN PATENT DOCUMENTS

FR    2645965    10/1990
JP    A 2006-90813    4/2006
(Continued)

OTHER PUBLICATIONS

EP Supplementary Search Report, 14836168.6-1554 /3033157 , dated Mar. 24 2017, pp. 14.
(Continued)

*Primary Examiner* — Benjamin L Lebron
(74) *Attorney, Agent, or Firm* — Barry Gaiman

(57) ABSTRACT

A lattice and distribution network for a stackable chromatography cassette comprising:
  a peripheral seal;
  at least one screen forming the lattice surrounded by the peripheral seal, each at least one screen comprising a plurality of struts in a latticed arrangement;
  a first internal distribution network fluidly coupled to the lattice and surrounded by the peripheral seal;
  a second internal distribution network disposed opposite the first internal distribution network, fluidly coupled to the lattice and surrounded by the peripheral seal;
  wherein a direction of fluid flow is established from the first internal distribution network through the lattice to the second internal distribution network; and
  wherein preferential streamlines are minimized.

20 Claims, 11 Drawing Sheets

Related U.S. Application Data

Aug. 12, 2014, now Pat. No. 9,599,594, which is a continuation-in-part of application No. 13/964,726, filed on Aug. 12, 2013, now Pat. No. 9,120,037, which is a continuation-in-part of application No. 13/013,807, filed on Jan. 25, 2011, now Pat. No. 8,506,802.

(60) Provisional application No. 62/307,467, filed on Mar. 12, 2016, provisional application No. 61/979,105, filed on Apr. 14, 2014, provisional application No. 61/297,896, filed on Jan. 25, 2010.

(51) Int. Cl.

| | | |
|---|---|---|
| *B01D 15/22* | (2006.01) | |
| *B01J 20/282* | (2006.01) | |
| *B33Y 10/00* | (2015.01) | |
| *B33Y 80/00* | (2015.01) | |
| *B01J 20/281* | (2006.01) | |
| *G01N 30/50* | (2006.01) | |
| *G01N 30/60* | (2006.01) | |
| *G01N 30/52* | (2006.01) | |
| *B01J 20/28* | (2006.01) | |

(52) U.S. Cl.
CPC ............... *B33Y 10/00* (2014.12); *B33Y 80/00* (2014.12); *G01N 30/482* (2013.01); *G01N 30/52* (2013.01); *G01N 30/6043* (2013.01); *G01N 30/6047* (2013.01); *B01J 20/282* (2013.01); *B01J 20/28016* (2013.01); *B01J 20/28042* (2013.01); *G01N 30/6069* (2013.01); *G01N 30/6095* (2013.01); *G01N 2030/527* (2013.01); *G01N 2030/528* (2013.01)

(58) Field of Classification Search
CPC ......... G01N 30/6095; G01N 2030/528; G01N 2030/527; B01D 15/206; B01D 15/22; B01D 15/1842; B01J 20/28028; B01J 20/282; B01J 20/28033; B01J 20/28042; B01J 20/28016; B33Y 80/00; B33Y 10/00
See application file for complete search history.

(56) References Cited

U.S. PATENT DOCUMENTS

| | | | |
|---|---|---|---|
| 4,971,736 A | 11/1990 | Hagen et al. | |
| 5,248,428 A * | 9/1993 | Hagen | B01D 39/00 210/198.2 |
| 5,800,706 A | 9/1998 | Fischer | |
| 7,947,175 B2 | 5/2011 | Shinkazh | |
| 7,988,859 B2 | 8/2011 | Shinkazh | |
| 9,599,594 B2 * | 3/2017 | de los Reyes | B01D 15/206 |
| 9,802,979 B2 | 10/2017 | Bracewell et al. | |
| 2001/0032814 A1 | 10/2001 | Kearney et al. | |
| 2003/0150806 A1 | 8/2003 | Hobbs et al. | |
| 2005/0006293 A1 | 1/2005 | Koehler | |
| 2007/0151924 A1 * | 7/2007 | Mir | B01D 61/14 210/637 |
| 2007/0151925 A1 * | 7/2007 | de los Reyes | B01D 61/14 210/641 |
| 2008/0135484 A1 | 6/2008 | Hammer | |
| 2008/0148936 A1 | 6/2008 | Baksh | |
| 2008/0236389 A1 | 10/2008 | Leedy et al. | |
| 2008/0283458 A1 | 11/2008 | Ishii | |
| 2009/0321338 A1 | 12/2009 | Natarajan | |
| 2010/0187167 A1 | 7/2010 | Reinbigler | |
| 2010/0222570 A1 | 9/2010 | Ratnam et al. | |
| 2011/0108522 A1 * | 5/2011 | Rozing | B01L 3/502753 216/54 |
| 2011/0206572 A1 | 8/2011 | McKenna et al. | |
| 2011/0217539 A1 | 9/2011 | Bonner et al. | |
| 2012/0097591 A1 | 4/2012 | Berthold | |
| 2012/0118807 A1 | 5/2012 | Natarajan | |
| 2012/0309053 A1 | 12/2012 | Wellings | |
| 2013/0020263 A1 | 1/2013 | Gebauer | |
| 2013/0068671 A1 | 3/2013 | Gebauer | |
| 2016/0257033 A1 * | 9/2016 | Jayanti | B29C 64/40 |

FOREIGN PATENT DOCUMENTS

| | | |
|---|---|---|
| JP | A2014-032134 | 2/2014 |
| WO | WO 90/05018 | 5/1990 |
| WO | WO 92/03206 | 3/1992 |
| WO | WO 2012/104278 | 8/2012 |

OTHER PUBLICATIONS

JP Office Action dated Oct. 16, 2018, Japanese Patent Application No. 2017-006413, 10 Pages.

International Search Report and the Written Opinion, PCT/US2014050743, dated Nov. 20, 2014, pp. 10.

Maksimova, E.F., et al. "Methacrylate-based monolithic layers for planar chromatography of polymers," Journal of Chromatography A, 1218: 2425-2431 (2011). Available online Dec. 21, 2010.

Svec, F., et al. "Molded rigid monolithic porous polymers: an inexpensive, efficient, and versatile alternative to beads for the design of materials for numerous applications," Ind. Eng. Chem. Res., 38: 34-48 (1999).

Siwak, M., et al. "Integration of a novel modular chromatography scaffold and resin design to achieve a Hyper Productive Protein A capture process". PowerPoint slides. Presented at ACS BIOT San Diego, Mar. 13-17, 2016.

* cited by examiner

Direction of flow 150

Direction of flow 150

Direction of flow 150

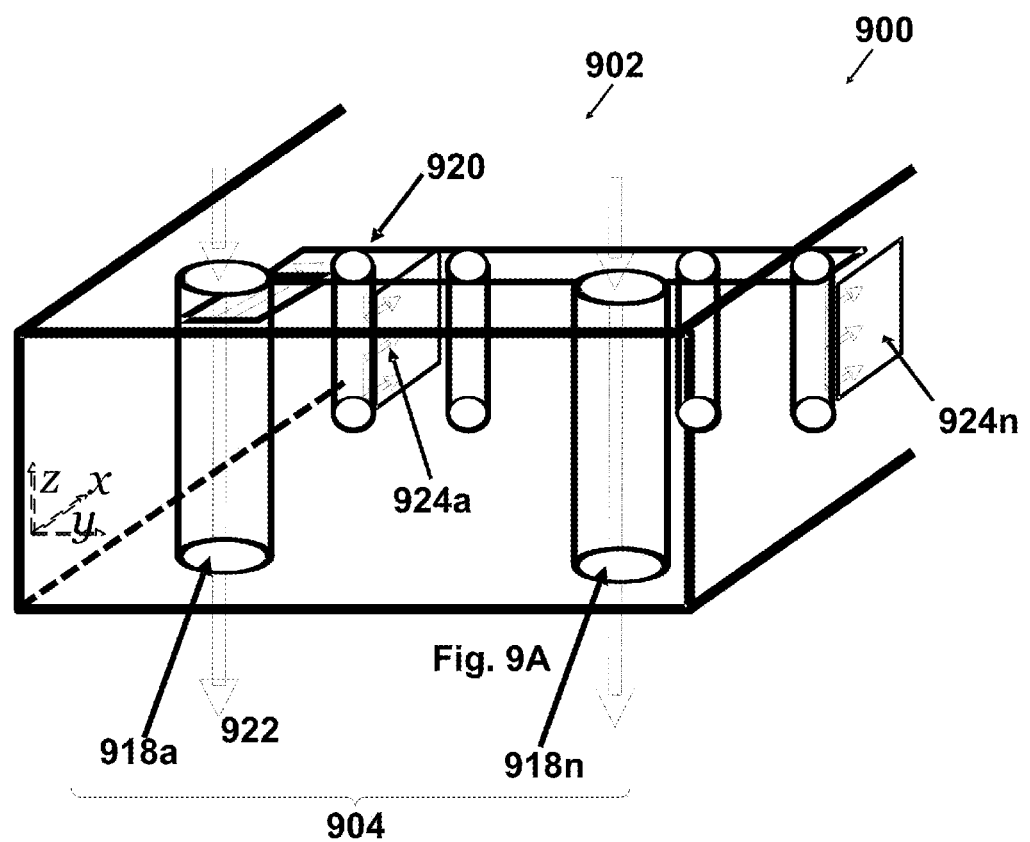
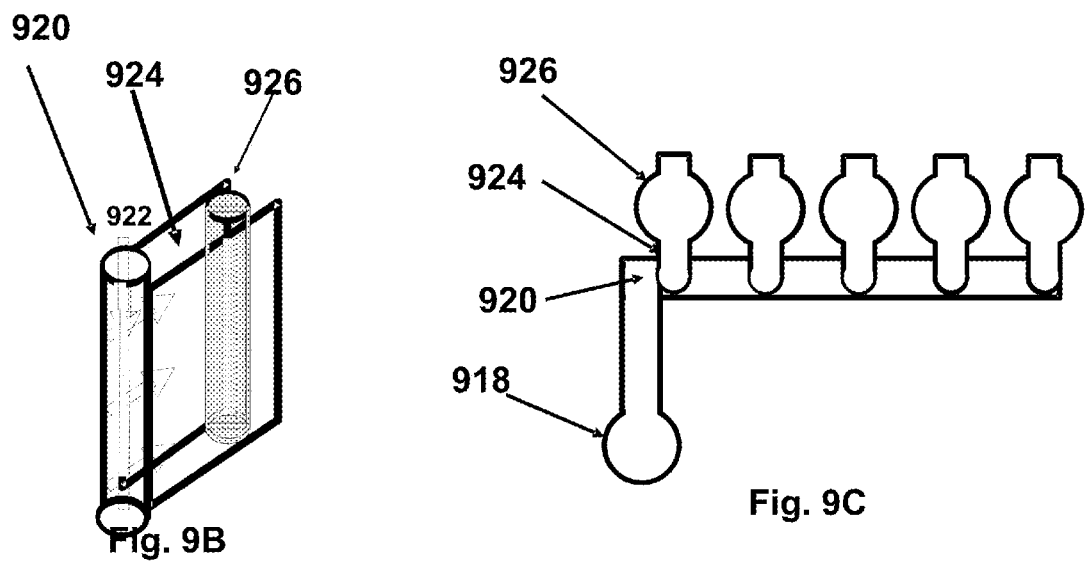

STACKABLE PLANAR ADSORPTIVE DEVICES

RELATED APPLICATIONS

This application claims the benefit of U.S. Provisional Application No. 62/307,467, entitled STACKABLE PLANAR ADSORPTIVE DEVICES, filed Mar. 12, 2016 and is a Continuation-in-part of pending application Ser. No. 14/907,804 filed Jan. 26, 2016, entitled STACKABLE PLANAR ADSORPTIVE DEVICES, now U.S. Pat. No. 9,599,594, granted Mar. 21, 2017, which claims the benefit of U.S. Provisional Application No. 61/979,105, filed Mar. 12, 2016; application Ser. No. 14/907,804 is a National Stage Entry of application Ser. No. PCT/US2014/050743 filed Aug. 12, 2014 which claims the benefit of U.S. Provisional Application No. 61/979,105, filed Apr. 14, 2014, and which is a Continuation-in-part of application Ser. No. 13/964,726, filed Aug. 12, 2013, now U.S. Pat. No. 9,120,037, granted Sep. 1, 2015, which applications are hereby incorporated herein by reference in their entireties.

TECHNICAL FIELD

The field of this invention is related to adsorptive devices and processes, of which chromatography is an example. More specifically, this invention relates to devices having adsorptive beds.

BACKGROUND OF THE INVENTION

Adsorptive processes and devices are widely used in the analysis and purification of chemicals, including synthetic and naturally-derived pharmaceuticals, blood products and recombinant proteins.

Chromatography is a general separation technique that relies on the relative affinity or distribution of the molecules of interest between a stationary phase and a mobile phase for molecular separation. The stationary phase typically comprises porous adsorptive media particles or microbeads imbibed with solvent. The mobile phase comprises a solvent, which can be aqueous or organic, that flows through the interstitial space that exists between the spaces occupied by the stationary phase.

Columns with associated end caps, fittings and tubing are the most common configuration, with the adsorptive media packed into the tube or column. The mobile phase is pumped through the column. The sample is introduced at one end of the column, the feed end, and the various components interact with the stationary phase by any one of a multitude of adsorptive phenomena. The differential adsorptive interaction between the components and media leads them to traverse the column at different velocities, which results in a physical separation of the components in the mobile phase. The separated components are collected or detected at the other end of the column, the eluent end, in the order in which they travel in the mobile phase. In one type of adsorptive process, referred to as capture and release process, the process involves multiple steps, first to load the media, then to wash it, and then to elute it.

Chromatographic methods include among other methods, gel chromatography, ion exchange chromatography, hydrophobic interaction chromatography, reverse phase chromatography, affinity chromatography, immuno-adsorption chromatography, lectin affinity chromatography, ion affinity chromatography and other such well-known chromatographic methods.

Adsorptive media come in many forms, most typically in the form of microparticles or microbeads (hereafter "beads"). The beads are conventionally packed into columns, with the column walls and ends immobilizing the beads into a fixed adsorptive bed, a bed being a porous three dimensional structure containing the stationary phase (in this case the beads with their pore space) and the pore space through which the mobile phase flows/permeates (the space between the beads, the interstitial space). Adsorptive media may also be formed into cohesive beds that retain their shape by virtue of the cohesion in the media; just like beds made with beads, these beds have two distinct regions, one occupied by the stationary phase and another occupied by the mobile phase; this type of media is referred to as monolithic media, or simply as monoliths. Media may also be formed in the shape of fabrics or webs, which can be stacked to form an adsorptive bed. Beds made of monoliths are cohesive in 3 dimensions, whereas beds made of webs are cohesive only in 2 dimensions; beds made of beads alone have no cohesion, requiring the column to maintain its shape.

Planar adsorptive processes and devices have been in use. Examples of planar adsorptive processes are paper chromatography and thin layer chromatography. In these processes, the adsorptive bed has a planar geometry in contrast to the cylindrical geometry of conventional chromatography beds. The mobile phase typically flows through the stationary phase by virtue of the capillarity of the porous medium, which draws the solvent into the porous space of the media. These processes do not require that the fluid pressure be contained since the fluid is not being pumped. More recently, a form of planar chromatography has been developed in which the fluid is pumped; this process is referred to as over-pressure planar chromatography (OPPC). OPPC requires that the media be contained in apparatus that maintains the shape of the bed in spite of the pressures used. In all cases, the planar adsorptive beds used in these processes are very thin, usually no thicker than a millimeter, making them suitable for analytical applications.

Furthermore, the bed depth, or adsorptive bed height, important in purification steps requiring resolution, is limited in membrane-based devices due to the low hydraulic permeability of microporous membranes. Membrane absorptive media are expensive, because of the high cost of the membrane substrate and the challenges of functionalizing the membrane surface with absorptive chemistry. Finally, membrane-based adsorptive devices inherently have low capacity, and as a result membrane adsorption devices have found applicability primarily in "polishing" steps (e.g., virus and DNA removal, where the adsorptive load is negligible, rather than in the core capture/purification steps of the target therapeutic agent).

Conventional chromatographic devices require that beads must be packed into a column. The quality of this packing determines the performance of the adsorbing bed. This adds another source of variability to the chromatographic process and must be validated before use. Furthermore, beds packed with beads are prone to voiding, a phenomenon whereby the beads settle into a denser structure resulting in the creation of voids and in non-homogeneities in the packing density of the bed, all of which results in a deterioration of performance. This is especially true in columns packed with soft or semi-compressible beads such as agarose, polymethylmethacrylate (PMMA) and any other polymeric bead with significant internal porosity.

SUMMARY

The special demands imposed on pharmaceutical manufacturing processes make it highly desirable that such processes be easily scaled-up. In particular, there are many advantages to processes that can be scaled-up without having to reset or redevelop the processing conditions. Such processes are referred to in the industry as linearly-scalable processes; in essence, the parameters that define the separation process and operating conditions remain unchanged as the process moves from the laboratory bench (i.e., discovery), where the column can be as small as several milliliters, to the process development laboratory (e.g., columns of several liters), to clinical manufacturing, to large-scale manufacturing, where the chromatography column can be as large as several hundred liters. Existing chromatographic devices are not linearly scalable, their design and geometry requiring significant alterations as the device size increases, thereby introducing uncertainties and unwanted risks as processes evolve from drug discovery, to clinical trials, to small-scale and then to large-scale manufacturing.

In general it should be noted that good chromatographic practice dictates that the hold-up volume of the planar distributors should be small compared to that of the adsorptive block to which it is distributing or from which it is collecting fluid. Good adsorptive and chromatographic practice also dictates that all fluid streamlines have the same length and residence time in order to reduce the dispersion of an adsorptive bed. Branched distributors ensuring equal flow rate in each branch may be used to distribute the flow; distributors producing these conditions may be referred to as isoflow conditions.

Aspects of the present invention relate to absorptive devices that have the high capacity of beads and include a lattice and distribution network for a stackable chromatography cassette including: a peripheral seal; at least one screen forming the lattice surrounded by the peripheral seal, each at least one screen including a plurality of struts in a latticed arrangement; a first internal distribution network fluidly coupled to the lattice and surrounded by the peripheral seal; a second internal distribution network disposed opposite the first internal distribution network, fluidly coupled to the lattice and surrounded by the peripheral seal; where a direction of fluid flow is established from the first internal distribution network through the lattice to the second internal distribution network; and where preferred streamlines (flow paths having a preferential flow) are minimized. Such a lattice and distribution network for a stackable chromatography cassette allows operation at higher flow rates and pressures than can be achieved with conventional columns.

Other aspects of the present invention relate to linearly scalable devices and absorptive devices that provide the flexibility to develop new purification processes beyond the conventional batch chromatography processes. Implementations may include one or more of the following features: a lattice and distribution network where one screen is a first co-planar screen having a first set of the plurality of struts in a latticed arrangement disposed in one plane; and further including a second co-planar screen having a second set of the plurality of struts in a latticed arrangement disposed in a second different plane, the second co-planar screen staggered from the first co-planar screen in one of: a direction parallel to the direction of fluid flow; a direction perpendicular to the direction of fluid flow; and both a direction parallel to the direction of fluid flow and a direction perpendicular to the direction of fluid flow; a lattice and distribution network where the at least one screen is a bi-planar screen having a first set of the plurality of struts disposed in a first plane and a second set of the plurality of struts disposed in a second different plane.

The lattice may also include a first set of the plurality of struts in the first plane disposed at a lattice angle to the second set of the plurality of struts in the second different plane forming the latticed arrangement. The lattice and distribution network where the lattice further includes a plurality of bi-planar screens; and where the bi-planar screens are configured in one of: an aligned configuration, a staggered configuration with respect to adjacent bi-planar screens staggered in one of: a direction parallel to the direction of fluid flow, a direction perpendicular to the direction of fluid flow, and both a direction parallel to the direction of fluid flow and a direction perpendicular to the direction of fluid flow. The lattice and distribution network includes an angle of attack between the flow direction and the plurality of bi-planar screens which is off normal.

Other aspects of the present invention include: a lattice and distribution network where the lattice angle is 90 degrees and the angle of attack is 45 degrees; a lattice and distribution network where a strut cross-section of the plurality of struts is about 0.2 mm to about 1.0 mm wide and about 0.2 mm to about 1.0 mm high; a lattice may also include a planar spacing between each adjacent one of the plurality of struts of about 2 to about 10 times a width of the strut; and a lattice and distribution network further including a plurality of open cells formed by the lattice. A lattice may also include an adsorptive bed formed by filling the plurality of open cells with a plurality of adsorptive beads.

In other embodiments, a lattice supports evenly distributed streamlines through the adsorptive bed and streamlines having a very narrow residence time distribution. Other embodiment include: a lattice and distribution network where the adsorptive beads have an average diameter less than about 100 microns; a lattice and distribution network where a distance between pairs of the plurality of struts forming each of a plurality of open cells is larger than five average bead diameters of the plurality adsorptive beads; and a lattice and distribution network further including: a first plate disposed to cover the lattice and the peripheral seal.

The lattice may also include a second plate opposite the first plate, the lattice disposed between the first and second plates and surrounded on four sides by the peripheral seal; a pass through distribution network disposed between the first plate and the second plate, and where the pass through distribution network provides an evenly distributed flow among a plurality of stackable chromatography cassettes. Other aspects include: a lattice and distribution network where the first internal distribution network and the second internal distribution network include one of: a plurality of distribution channels; a plurality of multi-level distribution channels; and a plurality of tunnels; a lattice and distribution network where the multi-level distribution channels include at least one branched distributor; a lattice and distribution network where the at least one branched distributor is an isoflow distributor; and a lattice and distribution network where each of the plurality of the struts has one of: an ellipsoidal cross-sectional profile. The lattice may also include a rectangular cross-sectional profile.

Other aspects include: a lattice and distribution network where the peripheral seal and the first and second plate form a rectangular cuboid; a lattice and distribution network where a support capability of the lattice is characterized by a specific surface area defined as a wetted surface area of the lattice divided by a void volume of the lattice, greater than about 5 $cm^{-1}$; a lattice and distribution network where the specific surface area of the lattice is greater than 10 cm$^{-1}$; a lattice and distribution network where a feature size of the lattice (e.g., the cross-section of a strut forming a lattice) is smaller than 0.5 mm; and a lattice and distribution network where a flow path parallel to the direction of fluid flow intersects at least one of the plurality of struts.

Another aspect includes a method of making a lattice and distribution network. The method includes fabricating a lattice and distribution network using a 3-D printer having a feature size smaller than 1 mm. Chromatography cassettes described herein include Chromassette® cassettes manufactured by SPF Technologies, LLC of Somerville, Mass.

BRIEF DESCRIPTION OF DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings. The following drawings are illustrative of embodiments of the invention and are not meant to limit the scope of the invention as encompassed by the claims. Throughout the figures, same or similar reference numbers indicate same or similar elements.

FIGS. 9A, 9B and 9C show an internal distribution network having multi-level distribution channels including at least one branched distributor and a pass through distribution network according to embodiments disclosed herein;

DETAILED DESCRIPTION OF THE INVENTION

Figure 1A:
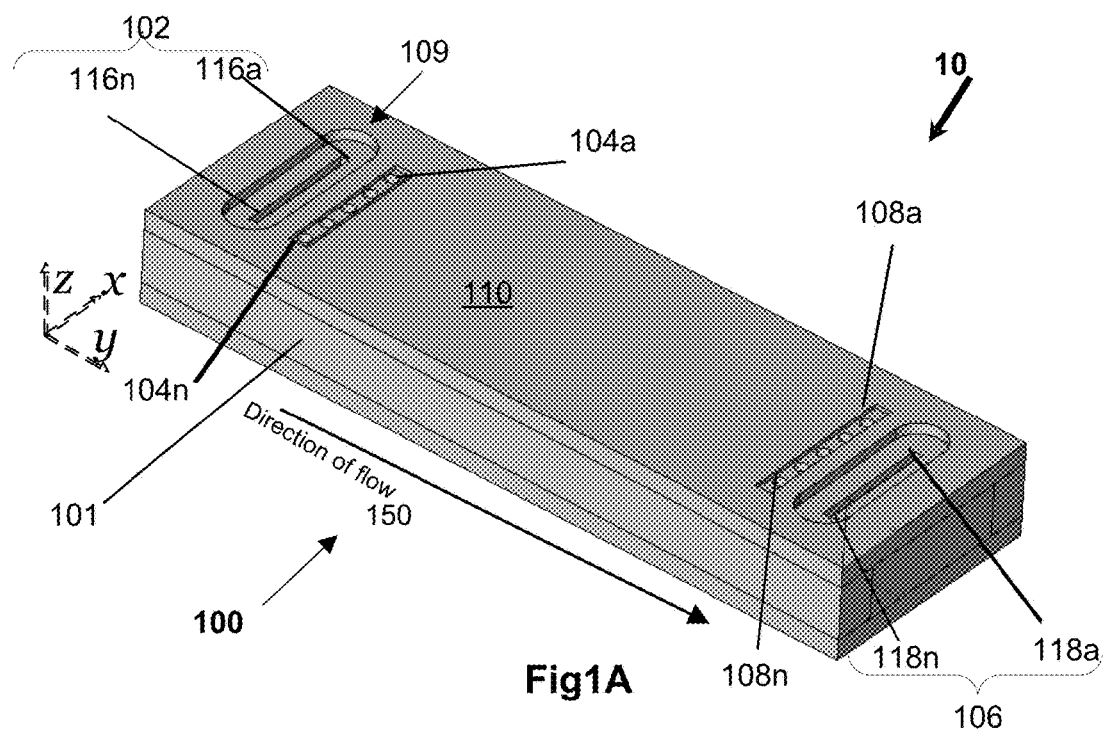
FIG. 1A is a view of a stackable chromatography cassette according to embodiments disclosed herein.

This invention generally relates to devices and processes suitable for preparative and manufacturing processes, and more specifically to processes used in the manufacture in the pharmaceutical industry for the production of medicinal or therapeutic products.

In contrast to conventional devices, applicants have discovered a way to support adsorptive media in a configuration that is linearly scalable and self supporting. Embodiments of the invention utilize planarly cohesive media. The cohesion plane of planarly cohesive media is oriented in parallel to the planar surfaces of the adsorptive device. The cohesiveness of the media along the cohesion plane enables the fabrication of adsorptive media blocks as described below.

The term adsorptive media, chromatography media, and media are herein used interchangeably to refer to the stationary phase of an adsorptive device; media can also refer to a single type of medium. As used herein, intimate contact generally refers to the scale of the void space left between adjacent screens, and means that these void spaces are of the same order of magnitude as the scale of the interstitial space occupied by the mobile phase within the beds. The term solvent and mobile phase are used herein interchangeably to refer to the mobile phase. The term lateral flow means fluid flow within the media along the cohesion plane; for example, in web-based adsorptive media lateral flow means flow along the plane of the web, in contrast to flow that is perpendicular to the plane of the web. The term adsorptive block and adsorptive device and cassette are used interchangeably to refer to the planarly cohesive beds of adsorptive media used in devices disclosed herein. The term isotropic means that the porous media through which the fluid flows has a homogeneous porous structure perpendicular to the direction of flow, such that the specific resistance to flow is independent of the location of the in the media in planes perpendicular to the direction of flow; the importance of isotropic media is elaborated upon further below. By substantially it is meant that the deviations of the values of the property being described are sufficiently small to enable the adsorptive device to perform as expected.

The geometrical symmetry that exists between the feed and effluent streams in the embodiments shown in FIGS. 2A-11B is conducive to conditions that generate streamlines of the same length. Additionally these embodiments have streamlines which intersect one or more struts which comprise the lattice such that there is no preferential streamline/flow path which includes only beads with no support from a lattice structure. Specifically, the first and second internal distribution networks are on opposite ends of the lattice. Such a geometrical and flow configuration, in conjunction with uniform hydraulic properties of the lattice and distribution network ensures that the flow streamlines within the adsorptive device have substantially the same length and residence time.

In other embodiments it may be advantageous to feed and collect all streams in either the top or bottom end plates, making the connectivity simpler and more convenient. In still other embodiments it may be advantageous to have the first and second distribution passageways on adjacent ends of the adsorptive devices (rather than on opposite ends) and possibly even on the same end. These situations do not conform to the symmetry that creates the isoflo condition and therefore, may not be optimal for chromatographic dispersion. However, the unfavorable impact of these non-optimal configurations on dispersion may be minimal, or tolerable, if the combined fluid volume of the distributors (i.e., the fluid volume of the distribution passageways plus the fluid volume of the planar distributors) is small compared to the total fluid volume of the adsorptive block; in some embodiments the combined fluid volume of the distributors is less than 10% of the fluid volume of the adsorptive block; in other embodiments the combined fluid volume of the distributors is less than 5% of the fluid volume of the adsorptive block. Therefore, such embodiments may still be useful.

Figure 1B:
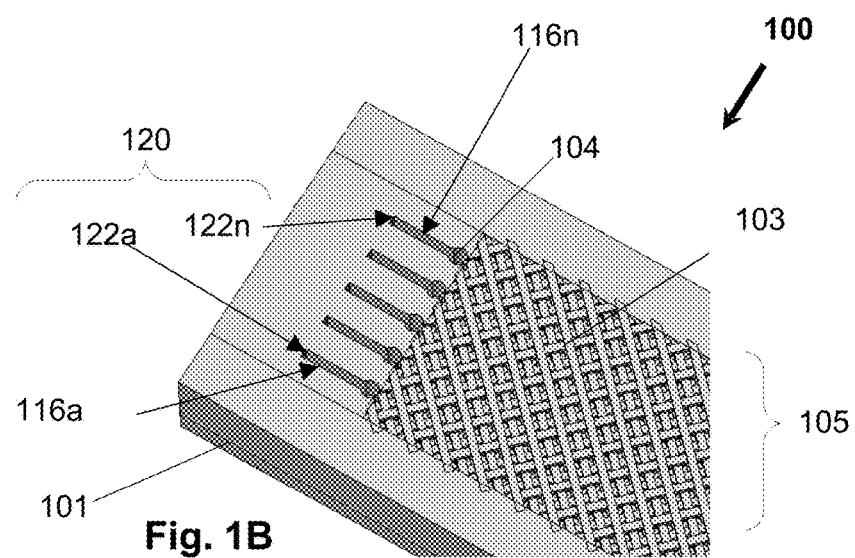
FIG. 1B is a view of a lattice and distribution network for a stackable chromatography cassette according to embodiments disclosed herein.

Now, referring to FIG. 1A, an exemplary stackable cassette 10 includes an exemplary lattice and distribution network 100 for a stackable chromatography cassette which includes a peripheral seal 101 and is described in more detail in FIG. 1B. The stackable cassette 10 further includes a top plate 110 (also referred to as first plate) and a bottom plate (not shown, also referred to as second plate) on opposite side of top plate. In one embodiment, the second plate is disposed opposite the first plate; the lattice is disposed between the first and second plates and is surrounded on four sides by the peripheral seal. In another embodiment, the peripheral seal 101 and the first plate (top plate 110) and second plate (bottom plate) form a rectangular cuboid.

The lattice and distribution network 100 includes first internal distribution network 102 including first internal distribution channels 116a-116n (collectively a first internal distribution channels 116) and second internal distribution network 106 including second internal distribution channels 118a-118n (collectively first internal distribution channels 118). The stackable cassette 10 provides access to the distribution channels 116 and 118 through the top plate 110 to provide distribution of feed stream and collection of eluent stream, respectively. The cassette's 10 lattice and distribution network 100 further includes passageways 104a-104n (collectively passageways 104) with access from the top plate 110 to accept packing retainers (not shown) on the feed end. The cassette's 10 second internal distribution network 106 further includes passageways 108a-108n (collectively passageways 108) with access from top plate 110 to accept packing retainers (not shown) on the eluent end. In this embodiment packing retainers are cylindrical porous rods having a circular cross-section with a diameter approximately equal to the diameter of passageways 104 and 108. Once inserted, the packing retainers are sealed and remain in place. Packing retainers with cross-sections different from a circle are possible. Cassette 10 also includes o-ring well 109 which with an o-ring (not shown) or other sealing mechanism seals the cassette 10 to a holder and also seals adjacent cassettes to each other when stacking multiple cassettes.

Now, referring to FIG. 1B, the exemplary lattice and distribution network 100 for a stackable chromatography cassette 10 of FIG. 1A includes the peripheral seal 101, at least one screen 103 forming a lattice 105 surrounded by the peripheral seal 101. The lattice and distribution network 100 further includes the first internal distribution network 102 and a second internal distribution network 106 (FIG. 1A) fluidly coupled to the lattice and surrounded by the peripheral seal 101. The first internal distribution network 102 and the second internal distribution network 106 are connected through the top plate 110 and bottom plate (not shown) to provide distribution of feed stream and collection of eluent stream, respectively. In this embodiment the first internal distribution network 102 and the second internal distribution network 106 also form a pass through distribution network 120 having channels 122a-122n, affecting distribution between cassettes and thereby enabling the stacking of the cassettes.

Figure 2A:
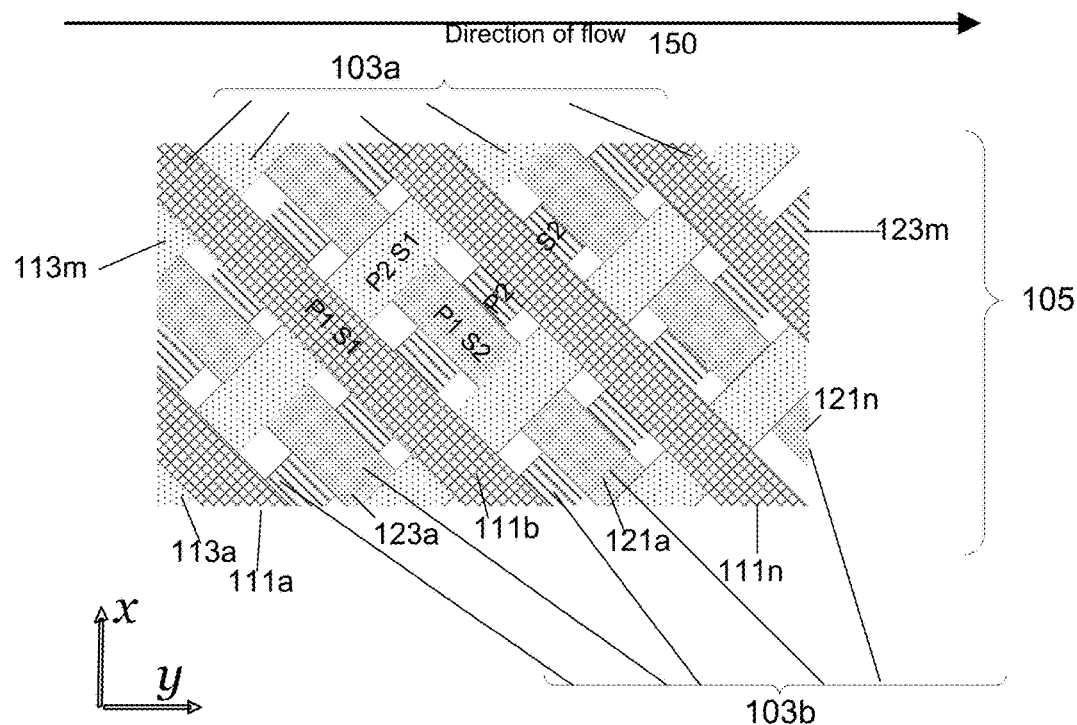
FIG. 2A is a top view of the bi-planar staggered lattice of FIG. 1B.

Now, referring to FIG. 2A where similar reference numbers represent similar element in FIG. 1B, an exploded top view of a portion of bi-planar lattice 105 shows additional details. Lattice 105 includes screens 103a (which include struts 111a-111n and struts 113a-113m) and 103b (which include struts 121a-121n and struts 123a-123m) surrounded by the peripheral seal 101 of FIG. 1B in a latticed arrangement. Here screen 103a includes a first set of struts 111a-111n and a second set of struts 113a-113m (collectively referred to as struts 111 and struts 113). Here screen 103b includes a first set of struts 121a-121n and a second set of struts 123a-123m (collectively referred to as struts 121 and struts 123). Screen 103a is referred to herein as bi-planar screens because strut 111b is disposed in one plane (indicated by P1S1—plane 1 screen 1) and strut 113a is disposed in a second plane (indicated by P2S1—plane 2 screen 1). Screen 103b (Screen2) is also a bi-planar screen including strut 121a disposed in one plane (indicated by P1S2—plane 1 screen 2) and strut 123a is disposed in a second different plane (indicated by P2S2—plane 2 screen 2).

Figure 2B:
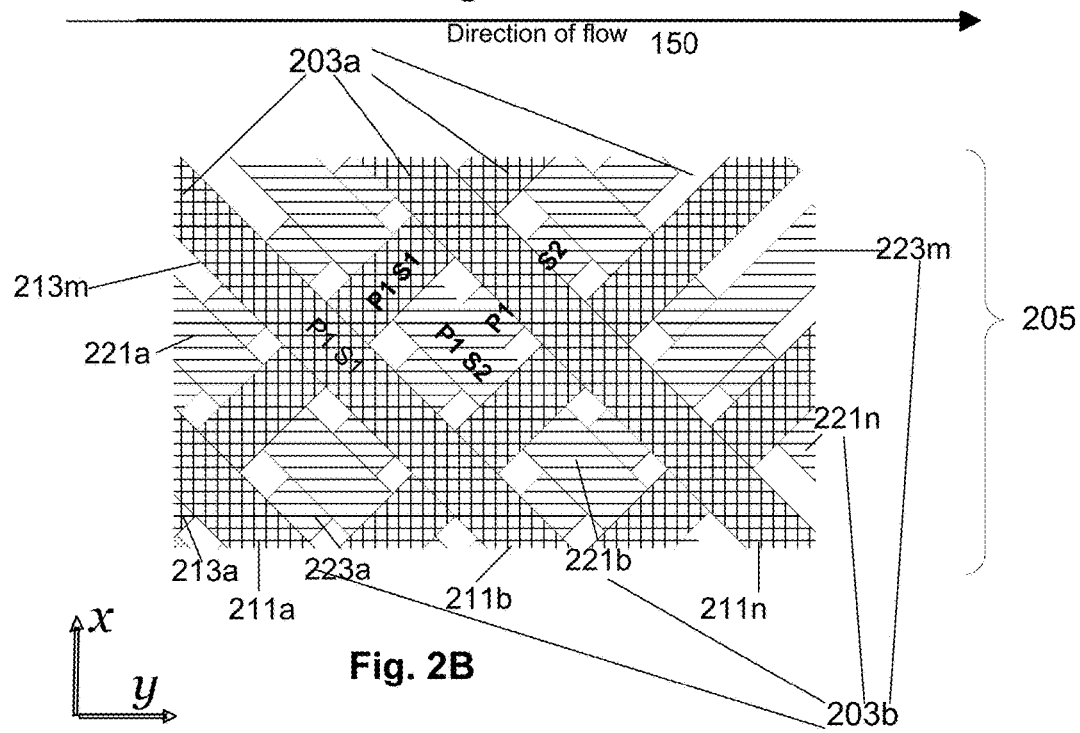
FIG. 2B is a top view of a co-planar staggered lattice according to embodiments disclosed herein.

FIG. 2B shows an exploded top view of a portion of co-planar lattice 205. Lattice 205 includes screens 203a-203b including struts in a latticed arrangement. Here screen 203a includes a first set of struts 211a-211n and a second set of struts 213a-213m (collectively referred to as struts 211 and struts 213). Here screen 203b includes a first set of struts 221a-221n and a second set of struts 223a-223m (collectively referred to as struts 221 and struts 223). Screen 203a is referred to herein as co-planar screens because strut 211b is disposed in the same plane (indicated by P1S1—plane 1 screen 1) as strut 213a (also indicated by P1S1—plane 1 screen 1). Screen 203b (Screen 2) is also a co-planar screen including strut 221a disposed in one plane (indicated by P1S2—plane 1 screen 2) and strut 223a is disposed in the same plane (indicated by P1S2—plane 1 screen 2).

Exemplary Lattice Configurations

The lattice configurations can be characterized by several parameters and attributes including:

Screen Configuration—for example co-planar where the lattice arrangement of struts is in a single plane (co-planar screen) or bi-planar where the lattice arrangement of struts is in two planes (bi-planar screen);

Strut width, height and length, and spacing between struts;

Lattice Angle which is generally an angle formed between the struts;

Aligned Configuration or Staggered Configuration with respect to adjacent bi-planar or co-planar screens which indicates whether adjacent screens are aligned or staggered in a direction parallel to the direction of fluid flow, staggered in a direction perpendicular to the direction of fluid flow and staggered in both a direction parallel to the direction of fluid flow and a direction perpendicular to the direction of fluid flow; and Angle of attack indicates the angle formed between the direction of flow and the struts in a plane or in a screen in the case of co-planar screens.

It is understood that there are many other lattice configurations and parameters to describe these configurations. For example, the lattices described in FIGS. 1A-5B and 11 have a repeated pattern wherein the struts have the same approximate cross-sectional dimensions and are spaced about equally; however, lattices with random spacing of the struts and random strut dimensions are also possible. An overall design goal is to provide optimized chromatographic performance based on the adsorptive media, the materials being processed and the process operating conditions Additionally struts can have various cross-sections including an ellipsoidal cross-sectional profile; or a rectangular cross-sectional profile, and can have varying cross-sectional dimensions. In one embodiment the cross-sectional dimension is less than about three mm, in other embodiments the cross-sectional dimension is less than about one mm.

Another way to characterize a support capability of the lattice is by a specific surface area of the lattice defined as the wetted surface area of the lattice divided by the void volume of the lattice. In one embodiment the specific surface area is greater than about 4 $cm^{-1}$. In other embodiments the specific surface area of the lattice is greater than 5 $cm^{-1}$, in other embodiments greater than 10 $cm^{-1}$, and in still other embodiments greater than 20 $cm^{-1}$.

Figure 3:
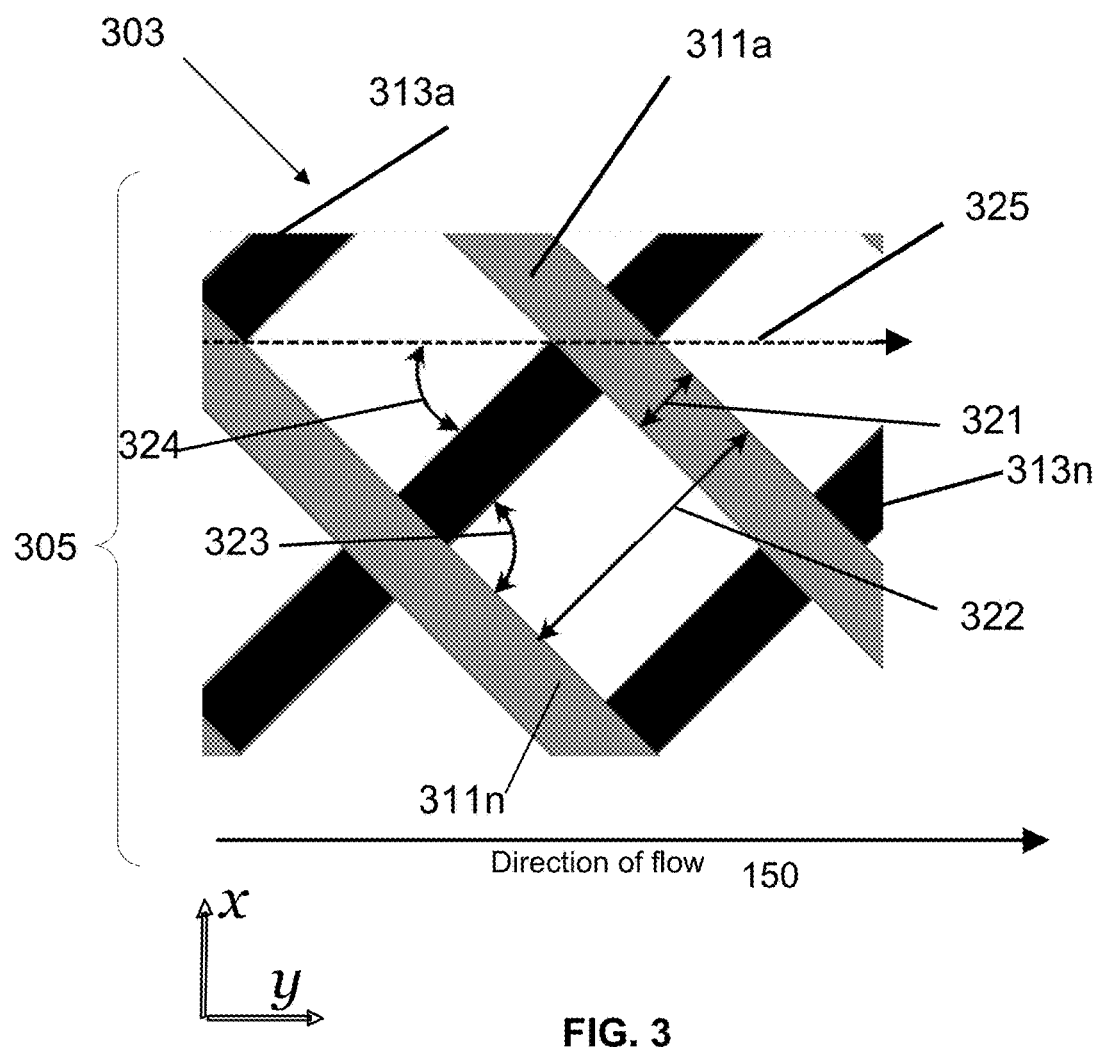
FIG. 3 is a is a top view of a bi-planar screen arranged showing various parameters according to embodiments disclosed herein.
Figure 5A:
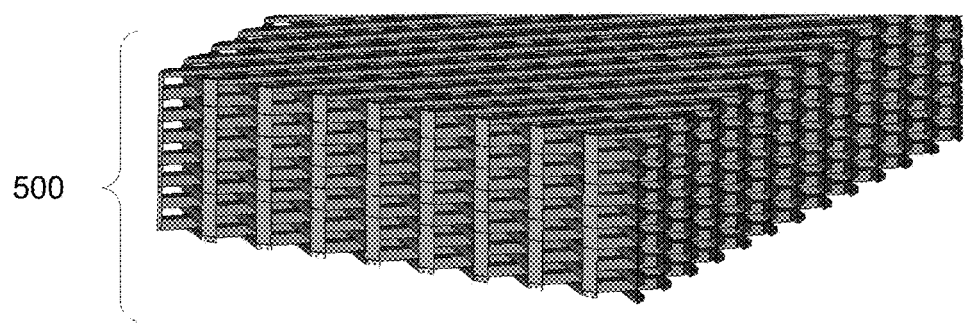
FIG. 5A is a view of a lattice having aligned bi-planar screens with a lattice angle of 90 degrees and an attack angle of 45 degrees according to embodiments disclosed herein.
Figure 5B:
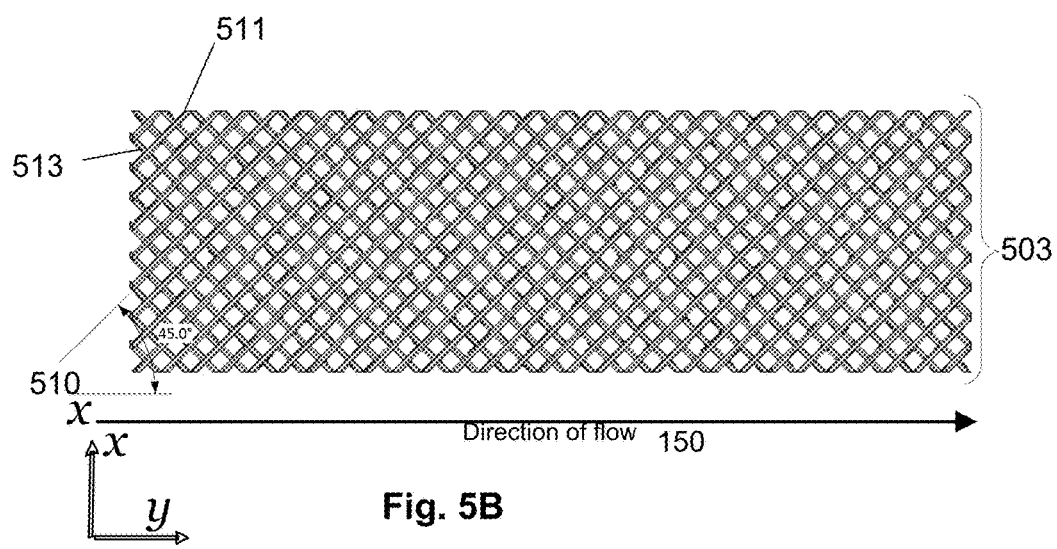
FIG. 5B is a top view of the lattice of FIG. 5A.

Now Referring to FIG. 3, a lattice 305 includes bi-planar screen 303. Each bi-planar screen 303 includes a first set of the plurality of struts 311a-311n disposed in a first plane and a second set of the plurality of struts 313a-313n disposed in a second different plane. Depending on the orientation of the struts of the lattice 305 to the direction of flow, flow pathways may not be interrupted by the lattice (these uninterrupted pathways are also referred to as preferred streamlines). This is less desirable for chromatographic separations since preferred streamlines become channels inducing preferential fluid flow. Those skilled in the art of chromatography know that such preferential fluid flow (also referred to as bypass) is undesirable. However, if the angle of attack between the struts and the fluid flow is changed the preferential streamlines are minimized. In contrast, lattice 500 shown in FIGS. 5A and 5B is also composed of bi-planar screens similar to lattice 105 of FIG. 2A, but in this case struts are oriented at 45° to the direction of flow eliminating the creation of such open channels or preferred streamlines.

It is possible to form lattices including stacked bi-planar screens 303. The bi-planar screens 303 can be staggered such that they are not aligned on top of each other. The staggering can be in the x or y dimensions, or alternatively in the direction parallel to the direction of fluid flow and a direction perpendicular to the direction of fluid, or both. In certain embodiments, flow paths parallel to the direction of fluid flow will intersect at least one of the plurality of struts 311 or 313. The screens may be bonded to each other at their contact points, or alternatively just stacked and not bonded. In more detail, the top view FIG. 3 shows bi-planar screen 303 formed by struts 311 in one plane and struts 313 at a lower plane. Struts 311 have a width 321, a height (not shown, perpendicular to the plane of the figure), and a spacing between struts 322. In this case, struts 313 have a similar width, height and spacing as struts 311. Struts 311 form a lattice angle 323 with struts 313, in this case about 90 degrees. Bi-planar screen 303 is oriented at angle of attack 324 between struts 313 and fluid flow direction (as shown by arrow 325), in this embodiment the angle of attack is about 45 degrees and the lattice angle 323 is about 90 degrees. In FIGS. 1A-5B and 11 the lattices shown have a lattice angle of about 90 degrees and an angle of attack of either 45 degrees or 0/90 degrees. However, other configurations having a lattice angle different from 90 degrees and an angle of attack different from 45 degrees are possible. For example, the configuration can be changed to accommodate different bead sizes, bead support requirements and bead materials.

Figure 4A:
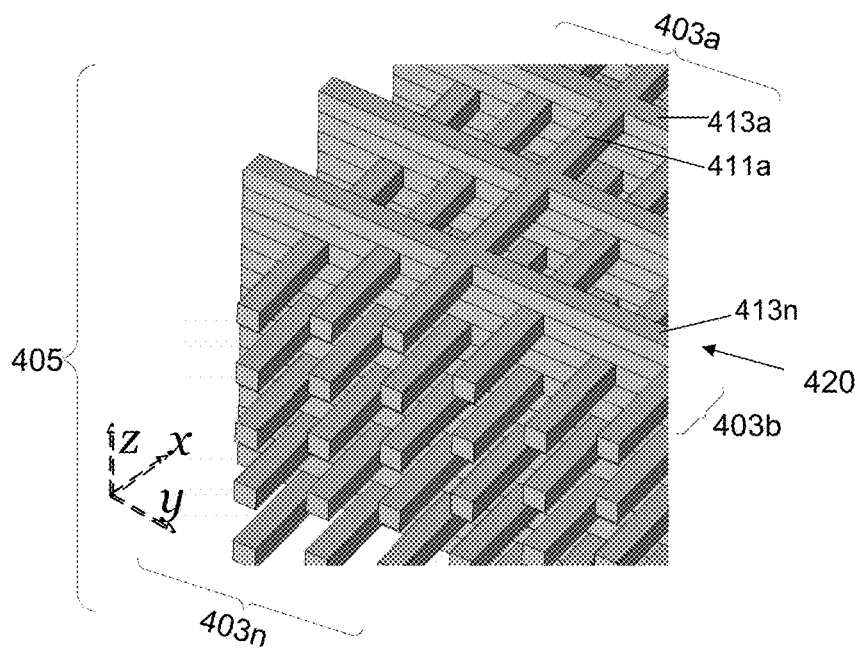
FIG. 4A is an isometric side view of an alternative lattice having co-planar screens arranged in a staggered in a y-direction and aligned in an x-direction according to embodiments disclosed herein.
Figure 4B:
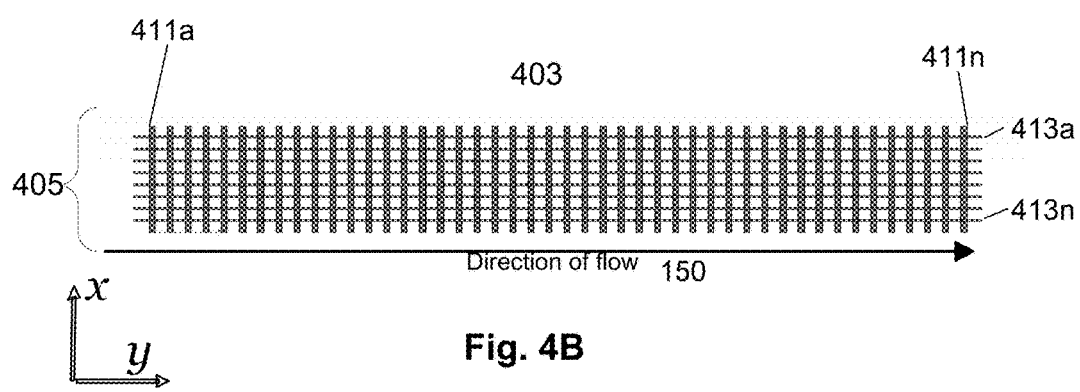
FIG. 4B is a top view of the alternative lattice of FIG. 4A.

Now Referring to FIGS. 4A and 4B, a lattice 405 includes co-planar screens 403a-403n (collectively referred to as co-planar screens 403) which are stacked on top of each other. Each co-planar screen 403 includes a first set of the struts 411a-411n and a second set of the struts 413a-413n arranged in a single plane. Here, the co-planar screens are staggered in the y-direction, but aligned in the x-direction, forming open cells along the y-axis. In other words, the first screen has the plurality of struts in a latticed arrangement disposed in one plane (co-planar screen 403a) and the second screen has the plurality of struts in a latticed arrangement disposed in a second different plane (co-planar screen 403b), the second co-planar screen is offset (i.e., staggered) from the first screen in the direction of flow (the y-direction). In one embodiment, the strut 411 or 413 cross-section is about 0.4×0.4 mm, spacing between co-planar screens 403 is about 2.4 mm and the staggered spacing is about 0.8 mm. This lattice configuration includes walls 420 formed by aligned struts 413.

In one embodiment, struts 411 and struts 413 are bonded to each other. In this embodiment, struts 411 and 413 have a rectangular cross-section and are spaced the same distance from each other; however, other cross-sections are possible, for example, circular or elliptical or combinations thereof. Furthermore, the lattice 403 has a regular "square" pattern wherein struts 411 are spaced apart the same approximate distance as struts 413 are spaced from each other. In this case the lattice 405 formed by the stacking of screens 403 is aligned in one direction (i.e., the screens are stacked in the same vertical location relatively to each other). However it is understood that other patterns are possible, including that struts may not be disposed in a regular pattern and that screens may be stacked such that the open cells formed by the adjacent screens are staggered (i.e., not aligned). Here lattice 405 minimizes preferential streamlines and have better chromatographic performance in contrast to lattices including parallel pathways where preferential streamlines of flow are possible.

It should be appreciated that many different patterns for the lattice 405 can be used, an important characteristic being that the lattice 405 includes an interconnected void space to accept the adsorptive beads, and that the size and density of the struts 411 and 413 need to be sufficient to provide the lattice and distribution network with sufficient strength to withstand the hydraulic forces during operation. Exemplary lattices have a void volume greater than 25%, greater than 50% and greater than 75%, and a Young's modulus in the x-y plane exceeding 50,000 psi, exceeding 100,000 psi and exceeding 200,000 psi. Furthermore, packing retainers may be inserted along the width of the device (i.e., along the x-coordinate) rather than along the height of the device (i.e., along the z-coordinate). In one embodiment, the packing retainers would be inserted from side-to-side rather than from top-to-bottom.

The cross-sectional dimensions and shape of the struts affect the specific surface area of the lattice, as well as the fraction of the total volume that is void volume vs. structural volume. In some embodiments the struts have a square or rectangular cross-sectional profile (the cross-section of the strut is commonly referred to as feature size) with a cross-sectional dimension less than 3 mm; in other embodiments the struts are less than one mm and in still other embodiments less than 0.5 mm in one or both cross-sectional dimensions. The size and shape of the struts may be limited by the fabrication technology used to fabricate the lattice, but struts can have any cross-sectional configuration. In one embodiment, the lattice and distribution network is fabricated using a 3-D printer having a feature size smaller than 1 mm.

Cassettes made with these lattices and having these configurations are easily scaled-up (or scaled-down) and are stackable, making them linearly scalable. The lattice configurations also provide: low extra-bed volume, a stable, robust bed even when packed with soft compressible beads, and the ability to operate at a high mobile phase velocity (e.g., greater than 500 cm/hr, and even greater than 1000 cm/hr).

Referring to FIGS. 5A and 5B lattice 500 comprises bi-planar screens 503 stacked on top of each other, and having an angle of attack 510 (also referred to as flow attack angle), in this case about 45 degrees. The screens are aligned at an "off normal" attack angle 510 (e.g., struts 511 are not parallel and struts 513 are not perpendicular to the direction of flow), here about 45 degrees, (i.e., the struts 511 and 513 are oriented at 45° to the direction of flow). An off normal attack angle means that struts 511 and 513 are lined up neither perpendicular nor parallel to the direction of flow so that a flow streamline through the lattice will intersect a strut 511 or strut 513. The off normal attack angle is also referred to as an oblique attack angle. This configuration minimizes the number of preferential streamlines and this configuration provides enhanced performance in terms of uniform residence time distribution of fluid flow because it is highly isotropic: all the streamlines through the lattice have a similar length. The off normal attack angle ensures that a flow path parallel to the direction of fluid flow intersects at least one of the plurality of struts; and the number of preferential streamlines is minimized. In this embodiment and similar embodiments, the size of the struts range from approximately 0.2 to 1 mm and the spacing between struts range from 0.5-4 mm. The lattice dimensions and configuration can be adjusted to accommodate various bead sizes and other physical characteristics for example: the co-planar screens can be staggered in a direction parallel to the direction of fluid flow (y direction), a direction perpendicular to the direction of fluid flow (x direction) and both a direction parallel to the direction of fluid flow and a direction perpendicular to the direction of fluid flow (both the x and y-directions).

Figure 6A:
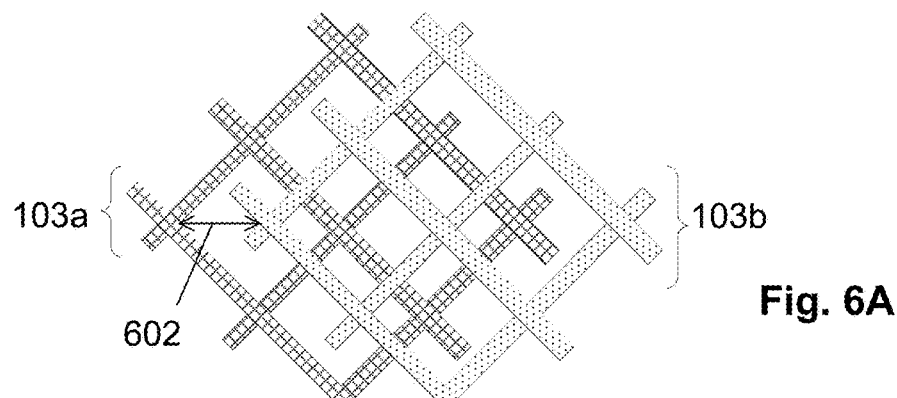
FIGS. 6A, 6B and 6C represent various staggered configurations.
Figure 6B:
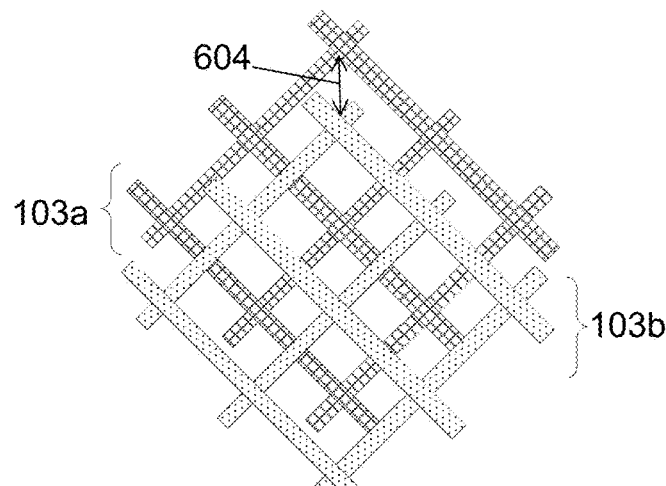
Figure 6C:
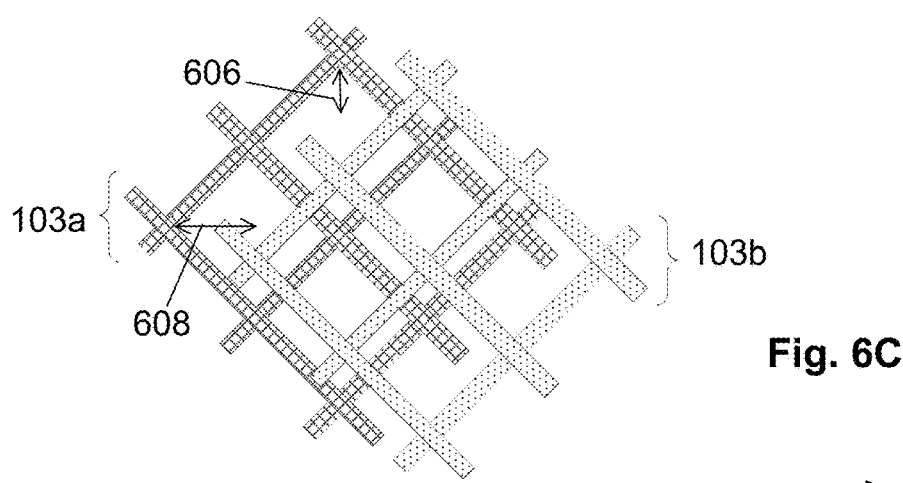

FIGS. 6A, 6B and 6C show some of the ways screens can be staggered to provide different streamlines through the adsorptive bed. FIG. 6A shows screens 103a and 103b staggered in a direction parallel to the direction of fluid flow, the staggered offset and direction indicated by double arrow 602. FIG. 6B shows screens 103a and 103b staggered in a direction perpendicular to the direction of fluid flow, the staggered offset and direction indicated by double arrow 606. FIG. 6C shows screens 103a and 103b staggered in both a direction parallel to the direction of fluid flow and a direction perpendicular to the direction of fluid flow the staggered offsets and directions indicated by double arrow 606 and 608.

Figure 7:
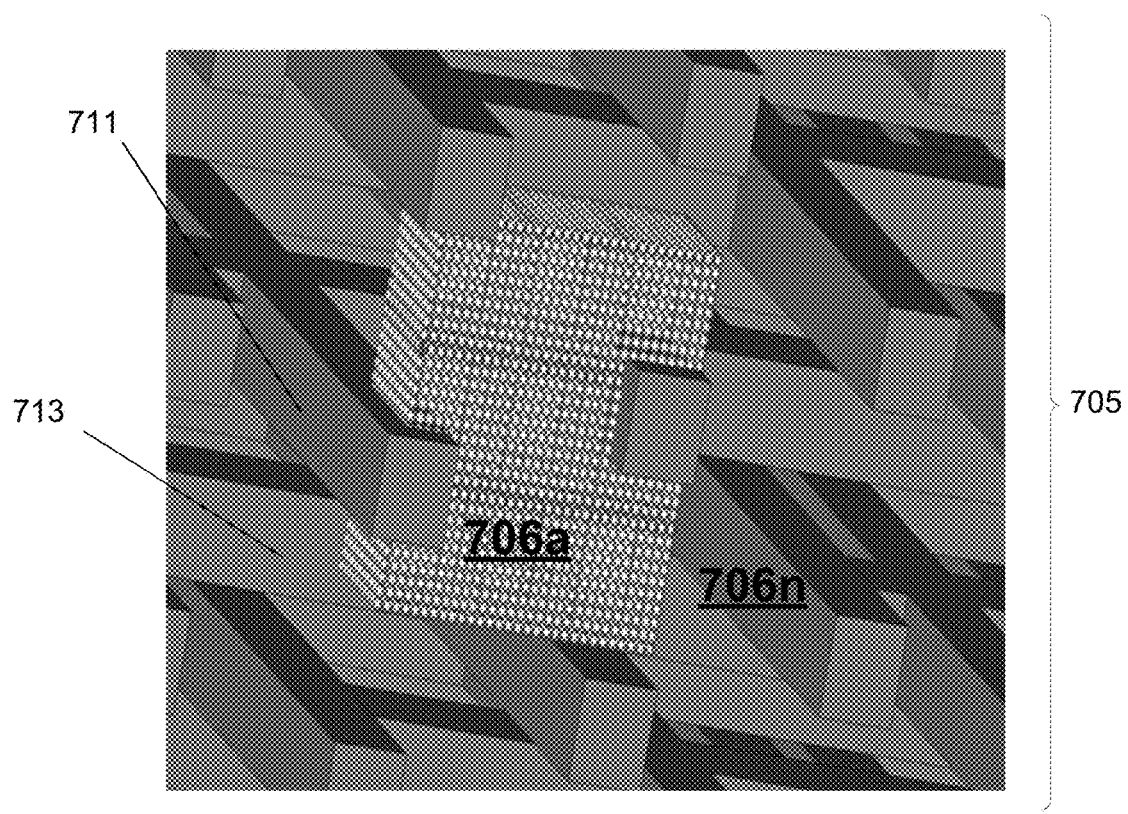
FIG. 7 shows open cells in a lattice with one cell packed with adsorptive beads according to embodiments disclosed herein.

Now referring to FIG. 7, lattice 705 of a lattice and distribution network includes open cells 706a-706n (collectively open cells 706) formed by a lattice 705. Here, open cell 706a is shown filled with adsorptive beads. An adsorptive bed is formed by filling the open cells with adsorptive beads, and the lattice 705 including struts 711 and 713 supports evenly distributed streamlines through the adsorptive bed. In one embodiment, the adsorptive beads have an average diameter less than about 100 microns. In another embodiment, the adsorptive beads have an average diameter less than about 50 microns. In still another embodiment, the adsorptive beads have an average diameter less than about 30 microns. The hardness of the beads can vary and the configuration of the lattice can be varied to provide the proper support for the adsorptive bed and to obtain streamlines through the lattice having a similar length.

In various embodiments, the Chromassette cassettes can be packed with any commercially available adsorptive bead, for example, Amsphere™ A2 and A3 Protein-A beads (JSR Corporation), MabSelect™ Sure Protein-A beads, SP Sepharose HP cation-exchange and Sepharose Q FF anion-exchange beads (GE Healthcare), YMC 25 & 75 µm cation-exchange beads (YMC Corporation), as well as 30 µm Q Fractogel anion-exchange beads (EMD Millipore Corporation). In one embodiment, on average the distance of any bead to the nearest strut or wall is approximately about 8 to about 20 average diameters of the plurality adsorptive beads "average bead diameter"). In another embodiment, a distance between pairs of struts forming each of the open cells is larger than about five average bead diameters.

Exemplary Distribution Network Configurations

Figure 8A:
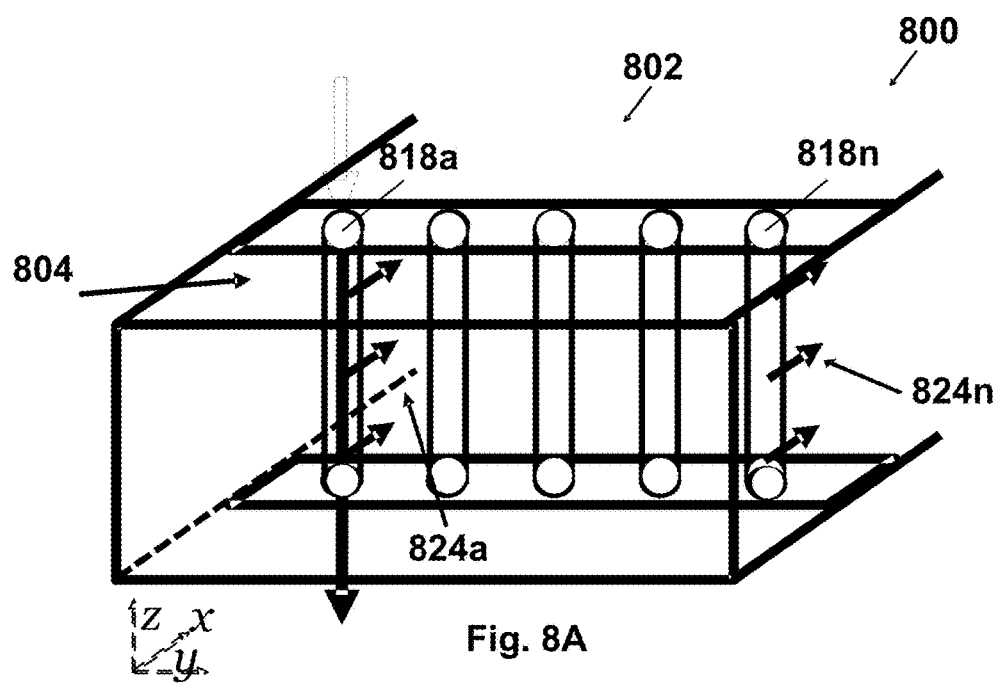
FIGS. 8A, 8B and 8C show an internal distribution network having a single level of distribution and a pass through distribution network according to embodiments disclosed herein.
Figure 8B:
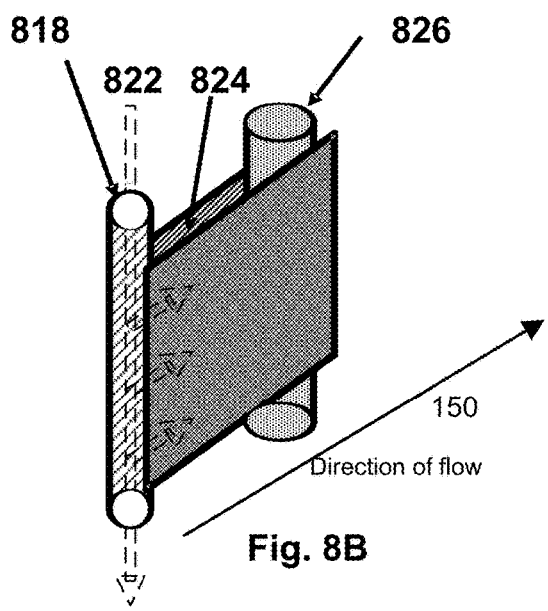

Now referring to FIGS. 8A and 8B, an exemplary lattice and distribution network 800 includes an internal distribution network 802 which includes distribution channels 824a-824n. The lattice and distribution network 800 also includes a pass through distribution network 804 having a plurality of pass through distribution passageways 818a-818n (collectively referred to as pass through distribution passageways 818). The pass through distribution passageways 818 are disposed between the first plate 110 (FIG. 1) and the second plate (not shown). Here the pass through distribution passageways 818 provides an evenly distributed flow among a plurality of stacked chromatography cassettes (not shown) and the feed to the internal distribution network 802. The internal distribution network 802 also includes passageways 826 for the insertion of packing retainers (e.g., frits). Arrow 822 indicates fluid flow through the internal distribution network 802 and arrow 150 indicates the direction of flow through the lattice.

Figure 8C:
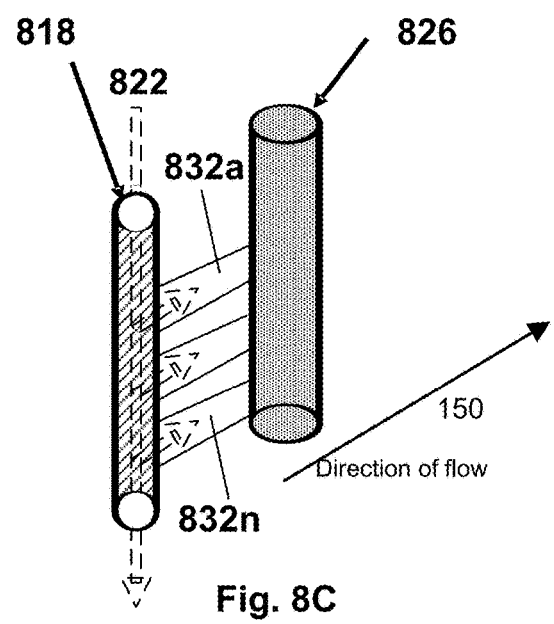

Referring to FIG. 8C, it is understood that the channels 824 can be replaced by multiple tunnels 832a-832n. A second internal distribution network on the opposite end of the lattice (not shown) is similar to the first internal distribution network 800 collecting the flow coming out of the lattice as the eluent.

Now referring to FIGS. 9A, 9B and 9C, an exemplary lattice and distribution network 900 includes an internal distribution network 902 which includes distribution channels 924a-924n and 920. The lattice and distribution network 900 also includes a pass through distribution network 904 having a plurality of pass through distribution passageways 918a-918n (collectively referred to as pass through distribution passageways 918). Here the pass through distribution passageways 918 provide an evenly distributed flow among a plurality of stackable chromatography cassettes (not shown) and the feed to the internal distribution network 902. In this embodiment distribution within a cassette is decoupled from distribution between cassettes. The internal distribution network 902 also includes passageways 926 for the insertion of packing retainers (e.g., frits). Arrow 922 indicates fluid flow through the internal distribution network 902.

Figure 10:
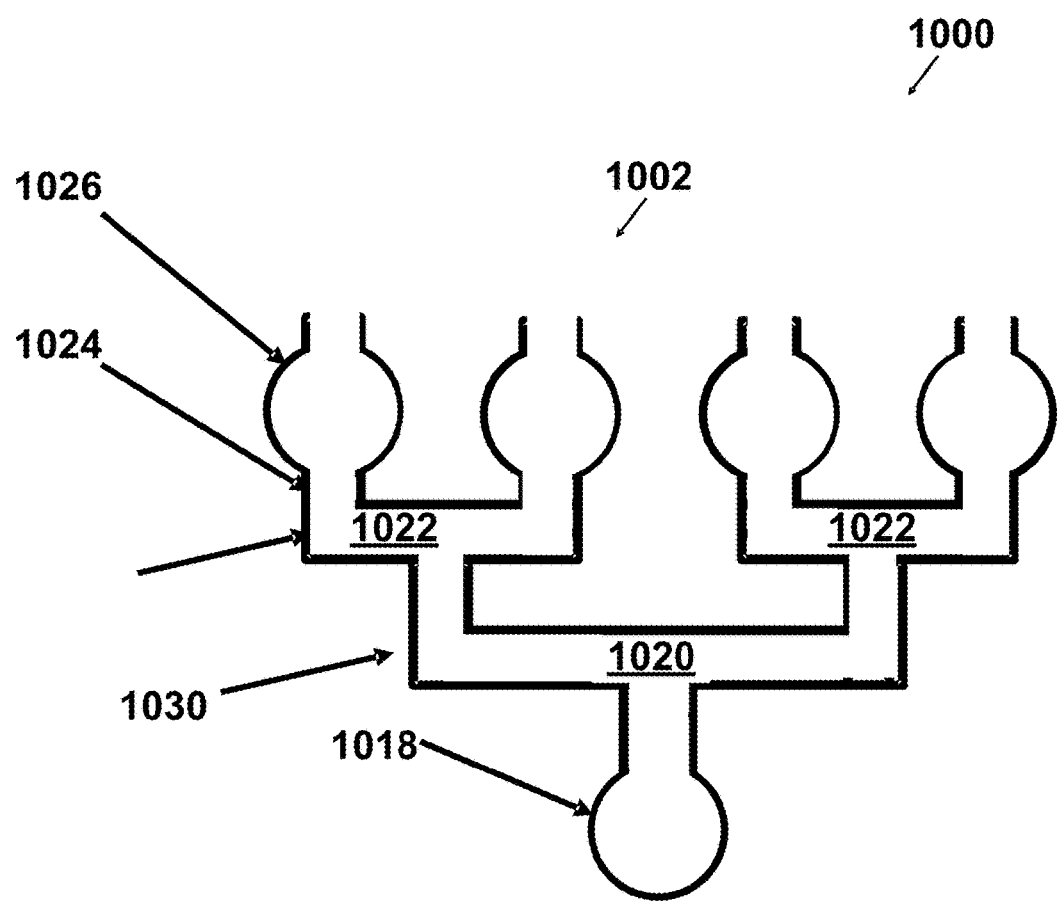
FIG. 10 shows internal distribution network of FIG. 9A where the branched distributor is an isoflow distributor.

Now referring to FIG. 10, a lattice and distribution network 1000 includes a first internal distribution network 1002 similar to the internal distribution network 902 of FIG. 9A. Here the branched distributor is a multilevel isoflow distributor 1030 having distribution levels 1020 and 1022. The distribution network 1002 more evenly distributes the feed stream through the lattice. The multilevel isoflow distributor 1030 includes the following advantages:
1. Hold up volume of multilevel isoflow distributor 1030 is much smaller.
2. The pass through distribution passageways 1018 can have larger diameters and lower pressure drop (ΔP) without increasing holdup volume.

The second internal distribution network (not shown) is similar to the first internal distribution network on the opposite end of the lattice.

Figure 11:
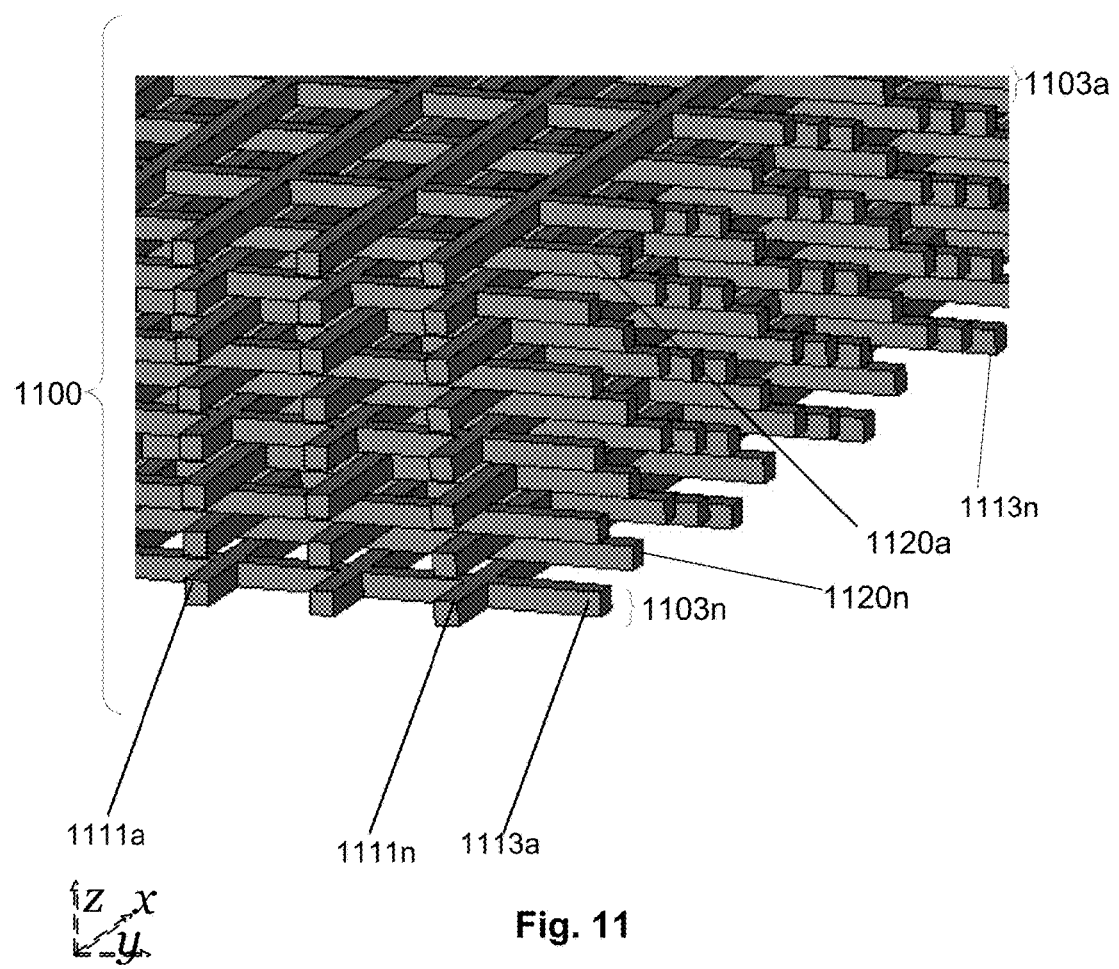
FIG. 11 is an isometric side view of an alternative lattice having co-planar screens arranged in a staggered pattern according to embodiments disclosed herein.

Now Referring to FIG. 11, a lattice 1100, similar to lattice 405 of FIG. 4A, additionally includes struts 1120a-1120n interspersed between the staggered coplanar screens 1103a-1103n. Unlike lattice 405, lattice 1100 does not form solid walls 420, resulting in a fully interconnected void space.

The lattice and distribution networks described herein not only provide support for the adsorptive bed but also provide planar cohesion in an x-y plane sufficient to withstand the operating pressures. The parameters of the screens and lattices can be varied for a particular application, bead size and adsorptive material or materials packed to form the adsorptive bed.

It is understood that although the embodiments described herein relate specifically to bio-molecular applications, the principles, practice and designs described herein are also useful in other applications, including the manufacture of vaccines and biopharmaceuticals. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. A lattice and distribution network for a stackable chromatography cassette comprising:
   a peripheral seal;
   at least one screen forming the lattice surrounded by the peripheral seal, each at least one screen comprising a plurality of struts in a latticed arrangement;
   a first internal distribution network fluidly coupled to the lattice and surrounded by the peripheral seal;
   a second internal distribution network disposed opposite the first internal distribution network, fluidly coupled to the lattice and surrounded by the peripheral seal;
   a plurality of open cells formed by the lattice;
   a packed adsorptive bed formed by filling the plurality of open cells with a plurality of adsorptive beads;
   wherein a direction of fluid flow is established from the first internal distribution network through the lattice to the second internal distribution network; and
   wherein flow paths having a preferential flow are minimized and evenly distributed through the adsorptive bed.

2. The lattice and distribution network of claim 1, wherein at the least one screen is a bi-planar screen having a first set of the plurality of struts disposed in a first plane and a second set of the plurality of struts disposed in a second different plane; and
   wherein the first set of the plurality of struts in the first plane are disposed at a lattice angle to the second set of the plurality of struts in the second different plane forming the latticed arrangement.

3. The lattice and distribution network of claim 2, wherein the lattice further comprises a plurality of bi-planar screens; and
   wherein the bi-planar screens are configured in one of:
      an aligned configuration;
      a staggered configuration with respect to adjacent bi-planar screens staggered in one of:
         a direction parallel to the direction of fluid flow;
         a direction perpendicular to the direction of fluid flow; and
         both a direction parallel to the direction of fluid flow and a direction perpendicular to the direction of fluid flow.

4. The lattice and distribution network of claim 3, wherein an angle of attack formed between the flow direction and each of the plurality of struts in each of the plurality of bi-planar screens is off normal.

5. The lattice and distribution network of claim 4, wherein the lattice angle is 90 degrees and the angle of attack is 45 degrees.

6. The lattice and distribution network of claim 1, wherein a strut cross-section of the plurality of struts is about 0.2 mm to about 1.0 mm wide and about 0.2 mm to about 1.0 mm high; and
   wherein a planar spacing between each adjacent one of the plurality of struts is about 2 to about 10 times a width of one of the plurality of struts.

7. The lattice and distribution network of claim 1, wherein the adsorptive beads have an average diameter less than about 100 microns.

8. The lattice and distribution network of claim 1, wherein a distance between pairs of the plurality of struts forming each of a plurality of open cells is larger than five average bead diameters of the plurality of adsorptive beads.

9. The lattice and distribution network of claim 1 further comprising:
   a first plate disposed to cover the lattice and the peripheral seal;

a second plate opposite the first plate, the lattice disposed between the first and second plates and surrounded on four sides by the peripheral seal;

a pass through distribution network disposed between the first plate and the second plate; and wherein the pass through distribution network provides an evenly distributed flow among a plurality of stackable chromatography cassettes.

10. The lattice and distribution network of claim 9, wherein the first internal distribution network and the second internal distribution network comprise one of:

a plurality of distribution channels;

a plurality of multi-level distribution channels; and a plurality of tunnels.

11. The lattice and distribution network of claim 10 wherein the multi-level distribution channels include at least one branched distributor.

12. The lattice and distribution network of claim 11 wherein the at least one branched distributor is an isoflow distributor.

13. The lattice and distribution network of claim 12, wherein each of the plurality of the struts has one of:

an ellipsoidal cross-sectional profile; and a rectangular cross-sectional profile.

14. The lattice and distribution network of claim 9, wherein the peripheral seal and the first and second plate form a rectangular cuboid.

15. The lattice and distribution network of claim 1, wherein a support capability of the lattice is characterized by a specific surface area defined as a wetted surface area of the lattice divided by a void volume of the lattice, greater than about three $cm^{-1}$.

16. The lattice and distribution network of claim 15, wherein the specific surface area of the lattice is greater than 10 $cm^{-1}$.

17. The lattice and distribution network of claim 1 wherein a feature size of the lattice is smaller than 0.5 mm.

18. The lattice and distribution network of claim 1 wherein a flow path parallel to the direction of fluid flow intersects at least one of the plurality of struts.

19. A method of making the lattice and distribution network of claim 1 comprising fabricating the lattice and distribution network using a 3-D printer having a feature size smaller than 1 mm.

20. The lattice and distribution network of claim 1, wherein the at least one screen is a first co-planar screen having a first set of the plurality of struts in a latticed arrangement disposed in one plane; and further comprising a second co-planar screen having a second set of the plurality of struts in a latticed arrangement disposed in a second different plane, the second co-planar screen disposed staggered from the first co-planar screen in one of:

a direction parallel to the direction of fluid flow;

a direction perpendicular to the direction of fluid flow; and both a direction parallel to the direction of fluid flow and a direction perpendicular to the direction of fluid flow.

* * * * *